(12) United States Patent
Wada et al.

(10) Patent No.: US 8,774,895 B2
(45) Date of Patent: Jul. 8, 2014

(54) ELECTROENCEPHALOGRAPHIC HEADSET

(75) Inventors: Seiji Wada, Kanagawa (JP); Takeshi Yamazaki, Kanagawa (JP); Natsuki Kimura, Tokyo (JP); Yoshihiro Wakita, Tokyo (JP); Koji Kashima, Kanagawa (JP); Tomiji Tanaka, Saitama (JP); Mitsuhiro Nakamura, Kanagawa (JP); Tatsumi Sakaguchi, Kanagawa (JP); Haruhiko Soma, Tokyo (JP); Takuro Yamamoto, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/616,185

(22) Filed: Sep. 14, 2012

(65) Prior Publication Data

US 2013/0085363 A1    Apr. 4, 2013

(30) Foreign Application Priority Data

Oct. 3, 2011 (JP) ................................. 2011-219132

(51) Int. Cl.
*A61B 5/0478* (2006.01)
*A61B 5/00* (2006.01)
(52) U.S. Cl.
CPC ............. *A61B 5/0478* (2013.01); *A61B 5/6803* (2013.01); *A61B 5/6814* (2013.01)
USPC ........................... 600/383; 600/396; 600/397

(58) Field of Classification Search
CPC ... A61B 5/0478; A61B 5/6803; A61B 5/6814
USPC ......................................... 600/383, 396, 397
See application file for complete search history.

(56) References Cited

U.S. PATENT DOCUMENTS

| | | | | |
|---|---|---|---|---|
| 3,998,213 A | * | 12/1976 | Price ............................. | 600/383 |
| 4,706,679 A | * | 11/1987 | Schmidt et al. ............... | 600/383 |
| 5,291,888 A | * | 3/1994 | Tucker ........................... | 600/383 |
| 5,293,867 A | * | 3/1994 | Oommen ....................... | 600/300 |
| 5,348,006 A | * | 9/1994 | Tucker .......................... | 600/383 |
| 5,479,934 A | * | 1/1996 | Imran ........................... | 600/544 |
| 6,067,464 A | * | 5/2000 | Musha .......................... | 600/383 |
| 8,463,354 B2 | * | 6/2013 | Fadem .......................... | 600/383 |
| 2005/0197556 A1 | * | 9/2005 | Stoler ........................... | 600/383 |
| 2010/0274153 A1 | * | 10/2010 | Tucker et al. ................. | 600/544 |

FOREIGN PATENT DOCUMENTS

| | | | |
|---|---|---|---|
| FR | 2627975 | * | 3/1988 |
| JP | 5-161621 | * | 6/1993 |
| JP | 10-165386 A | | 6/1998 |

* cited by examiner

*Primary Examiner* — Lee S Cohen
(74) *Attorney, Agent, or Firm* — Sony Corporation

(57) ABSTRACT

An electroencephalographic headset includes: a supporter that includes expanding and contracting wires each having expansion and contraction properties and is to be attached to a head of a user by expansion and contraction of each of the expanding and contracting wires; and a plurality of electrodes that are provided to the supporter in defined placement.

5 Claims, 9 Drawing Sheets

User $l1:l2:l3 = m1:m2:m3$

ELECTROENCEPHALOGRAPHIC HEADSET

BACKGROUND

The present disclosure relates to an electroencephalographic (EEG) headset for placing electrodes to be used for brain wave measurement on the head of a user.

Brain waves being electrical signals generating due to human brain activities can be measured by electrodes attached to a scalp of a user (subject). The brain waves to be measured depend on positions of the scalp and are measured with the electrodes being attached to defined positions of the scalp. Examples of electrode placement include electrode placement according to an international 10-20 system.

It is troublesome to place the electrodes in defined positions of the scalp for each brain wave measurement. A headgear-type electroencephalographic apparatus with electrodes being provided in defined positions in advance is often used. For example, Japanese Patent Application Laid-open No. HEI 10-165386 (hereinafter, referred to as Patent Document 1) discloses an electroencephalographic headgear with electrodes being placed in predetermined positions of a net cap to be put on the head of the user.

SUMMARY

However, in the electroencephalographic headgear described in Patent Document 1, the electrodes are placed in the predetermined positions, and hence there is a fear that contact positions of the electrodes may be inappropriate for some user's head sizes. Although it is described that the net cap is flexible, it is considered that whether or not the electrodes are placed in the defined positions depends on the head shape of the user and the electrode positions need to be adjusted for correct brain wave measurement.

In view of the above-mentioned circumstances, there is a need for providing an electroencephalographic headset that is easy to attach and capable of placing electrodes in correct positions.

According to an embodiment of the present disclosure, there is provided an electroencephalographic headset including a supporter and a plurality of electrodes.

The supporter includes expanding and contracting wires each having expansion and contraction properties and is to be attached to a head of a user by expansion and contraction of each of the expanding and contracting wires.

The plurality of electrodes are provided to the supporter in defined placement.

With this configuration, when the user wears the electroencephalographic headset, the expanding and contracting wires expand and contract corresponding to the head shape, and hence intervals of the electrodes are kept at original ratio. Therefore, irrespective of the head size of each user, it is possible to place the electrodes in the defined placement.

The supporter may be constituted of an annular frame to be placed around the head of the user, and the expanding and contracting wires that are radially connected to each other and are connected to the frame.

With this configuration, when the user wears the electroencephalographic headset, the expanding and contracting wires expand and contract and the electrodes are placed in the defined placement and it is possible to fix the electroencephalographic headset to the head of the user by the frame.

The supporter may be constituted of a head-fixing arm to be attached to the head of the user, and the expanding and contracting wires that are concentrically connected to the head-fixing arm.

With this configuration, when the user wears the electroencephalographic headset, the expanding and contracting wires expand and contract and the electrodes are placed in the defined placement and it is possible to fix the electroencephalographic headset to the head of the user by the head-fixing arm.

The electrodes may be each constituted of a core that is formed of silver/silver chloride with each of the expanding and contracting wires being a center axis, and an elastic member that is wound around the core in a cylindrical form and impregnated with an electrolytic solution.

With this configuration, when electrical contact between one of the electrodes and the scalp of the user is deteriorated, by rotating the electrode with the expanding and contracting wire being a rotation axis, it is possible to keep the electrical contact between the electrode and the scalp of the user.

The electroencephalographic headset may further include a driving unit configured to rotate one of the electrodes when electrical contact between the electrode and a scalp of the user is loose, the electrical contact being detected based on contact resistance of the electrode.

With this configuration, it is possible for the electroencephalographic headset to automatically keep the electrical contact between the electrodes and the scalp of the user.

The defined placement may be electrode placement according to an international 10-20 system, and the expanding and contracting wires may be connected corresponding to the electrode placement according to the international 10-20 system.

With this configuration, when the user wears the electroencephalographic headset, it is possible to realize the electrode placement according to the international 10-20 system.

As described above, according to the embodiment of the present disclosure, it is possible to provide an electroencephalographic headset that is easy to attach and capable of placing electrodes in correct positions.

These and other objects, features and advantages of the present disclosure will become more apparent in light of the following detailed description of best mode embodiments thereof, as illustrated in the accompanying drawings.

DETAILED DESCRIPTION OF EMBODIMENTS (First Embodiment)

An electroencephalographic headset according to a first embodiment of the present disclosure will be described.

[Configuration of Electroencephalographic Headset]

Figure 1:
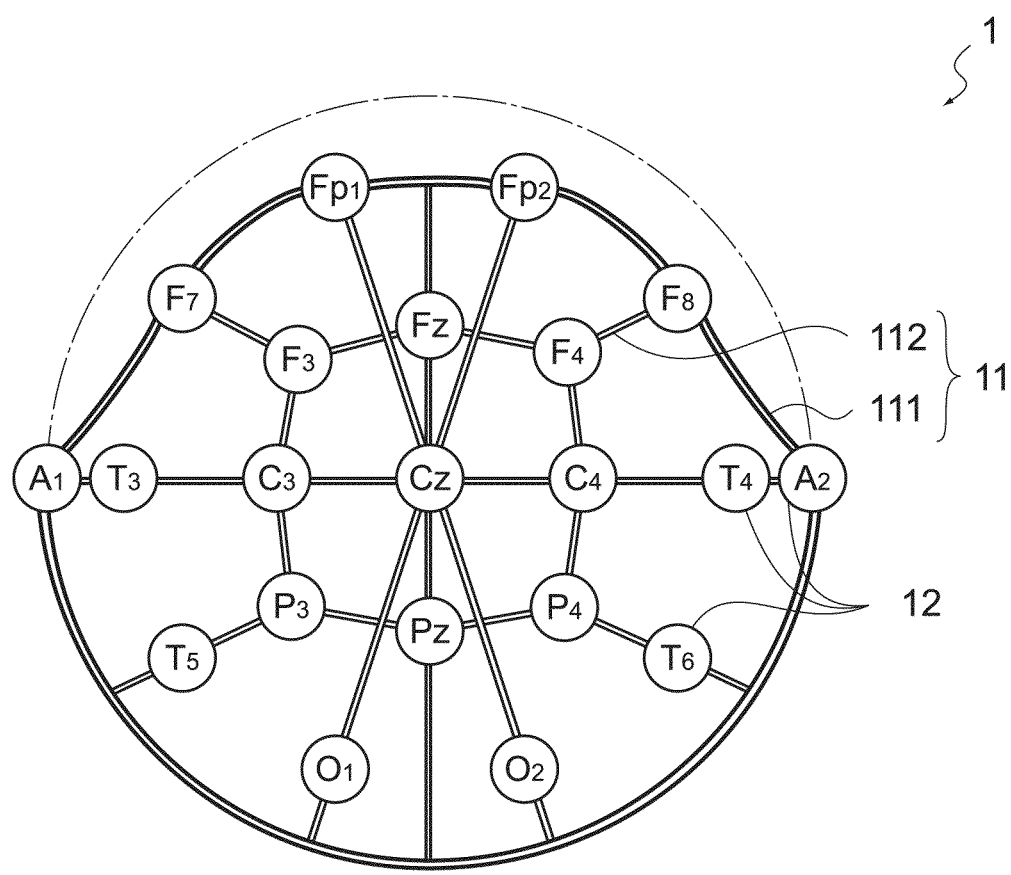
FIG. 1 is a schematic view showing a configuration of an electroencephalographic headset according to a first embodiment of the present disclosure.
Figure 2:
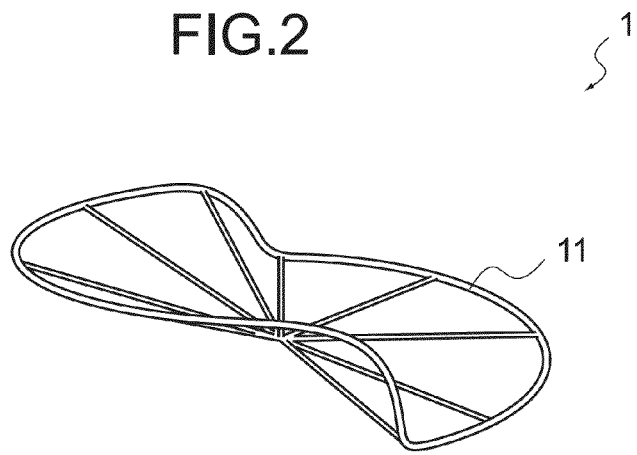
FIG. 2 is a schematic view showing a configuration of the electroencephalographic headset.
Figure 3:
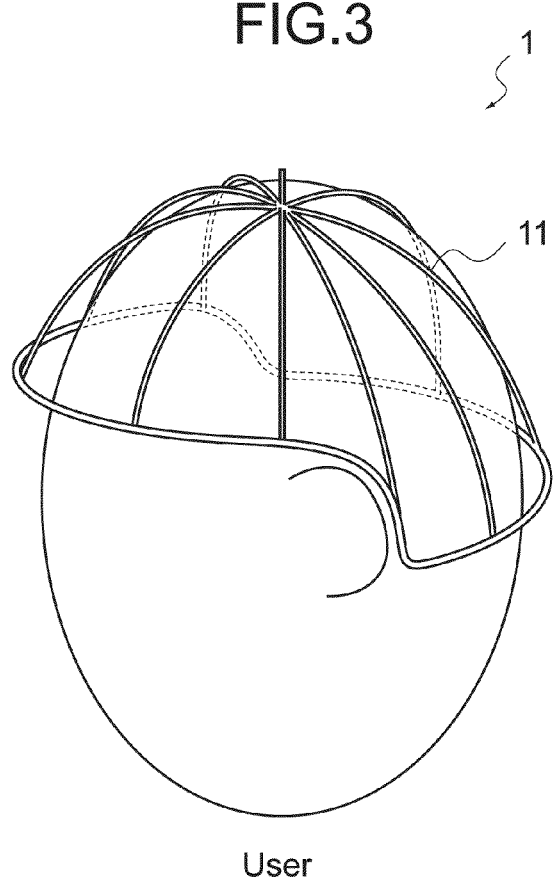
FIG. 3 is a schematic view showing a configuration of the electroencephalographic headset.

FIGS. 1 to 3 are views each showing a configuration of an electroencephalographic headset 1 according to the first embodiment of the present disclosure. FIG. 1 is a top view thereof, FIG. 2 is a side view thereof, and FIG. 3 is a schematic view of the electroencephalographic headset 1 attached to a user. As shown in those figures, the electroencephalographic headset 1 is constituted of a supporter 11 and electrodes 12. The supporter 11 is attachable to the head of the user. The plurality of electrodes 12 are provided in predetermined positions of the supporter 11. It should be noted that, in FIGS. 2 and 3, the electrodes 12 are omitted.

The supporter 11 is constituted of a frame 111 and expanding and contracting wires 112. The frame 111 is formed in a shape surrounding the head of the user and can be formed to be easily attached to the head by being curved from the back of the ears of the user. The frame 111 may have expansion and contraction properties or may have no expansion and contraction properties.

The expanding and contracting wires 112 are radially connected to each other and are each connected to the frame 111. Radial connection points of the expanding and contracting wires 112 may be located in positions corresponding to the parietal region of the user when the electroencephalographic headset 1 is attached to the head of the user. The expanding and contracting wires 112 can be connected corresponding to the electrode placement (international 10-20 system) shown in FIG. 1.

When attached to the head of the user as shown in FIG. 3, the thus formed supporter 11 is attached to the head of the user by expansion and contraction of the expanding and contracting wires.

Figure 4:
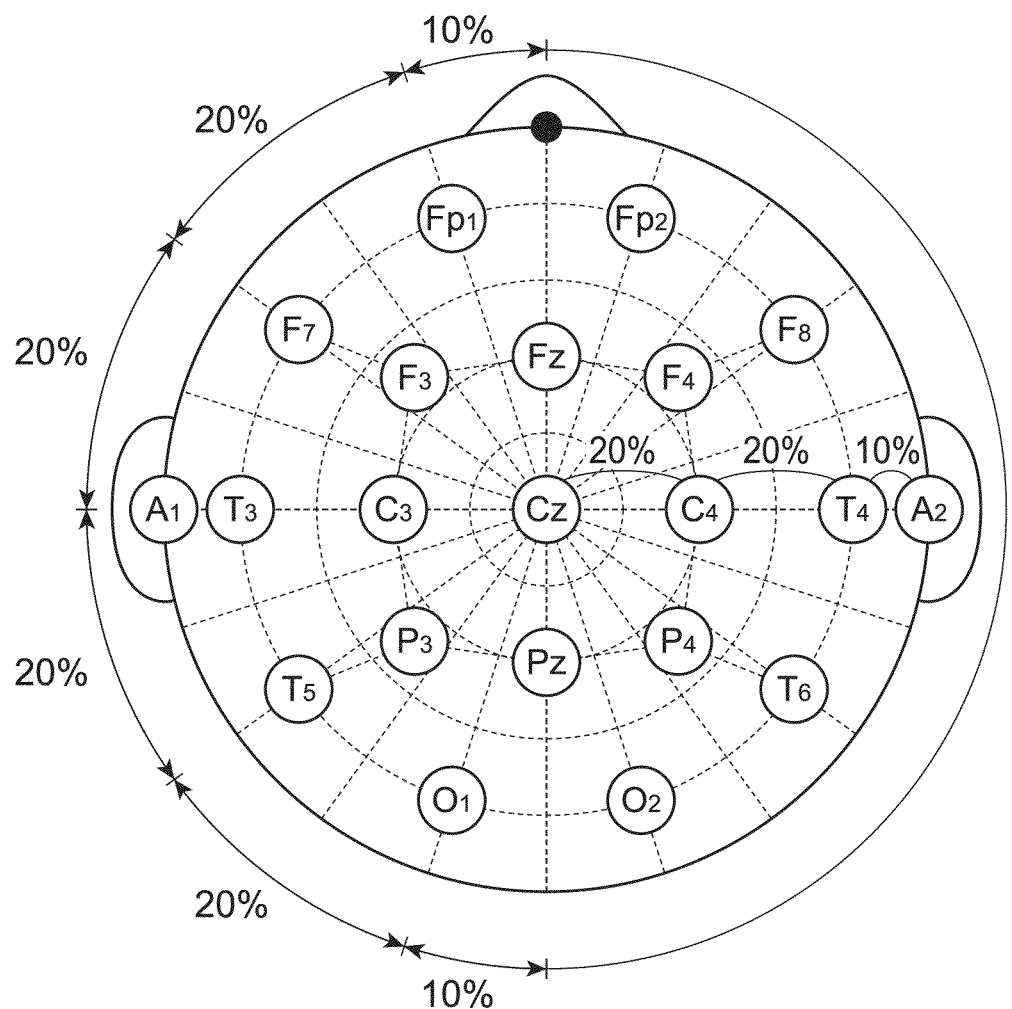
FIG. 4 is a schematic view showing electrode placement defined by an international 10-20 system.

The electrodes 12 are placed in defined positions on the supporter 11. Although not particularly limited, the electrode placement can be placement according to the international 10-20 system being standard electrode placement in current brain wave measurement that is shown in FIG. 4.

Figure 5:
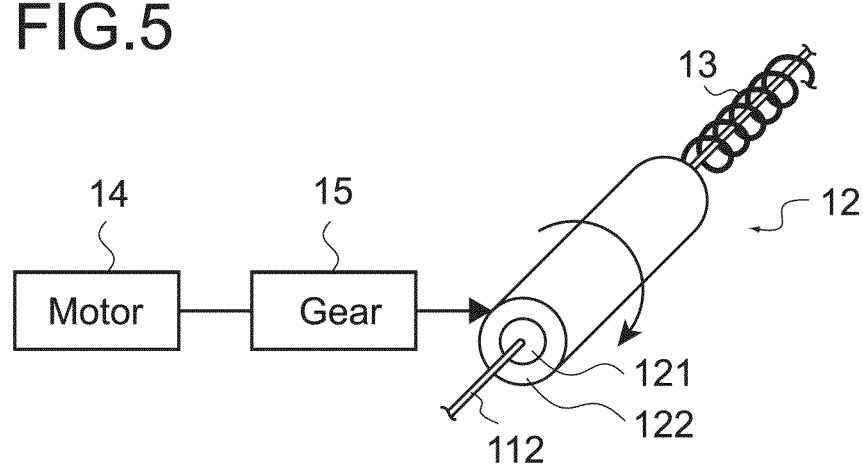
FIG. 5 is a schematic view showing a structure of an electrode of the electroencephalographic headset according to the first embodiment of the present disclosure.

Although not particularly limited, the electrodes 12 can be structured as follows. FIG. 5 is a schematic view showing a structure of one of the electrodes 12. As shown in the figure, the electrodes 12 may be each formed of silver/silver chloride and constituted of a core 121 with the expanding and contracting wire 112 being a center and an elastic member 122 wound around the core 121. The elastic member 122 may be formed of, for example, a liquid-holding material such as sponge and gel. The elastic member 122 is impregnated with an electrolytic solution (e.g., salt water) and keeps the core 121 in electrical contact with the scalp. A wiring 13 is connected to the core 121 and the wiring 13 is wound around the expanding and contracting wire 112. With such a structure, when the expanding and contracting wire 112 expands or contracts, the wiring 13 is prevented from interfering with the expansion or the contraction.

With this structure, the electrode 12 is capable of rotating on the scalp with the expanding and contracting wire being the center. Further, the contact surface with the scalp is changed and the sebum of the scalp is wiped off, so that the electrical contact can be ensured.

In addition, a motor 14 and a gear 15 can be connected to the electrode 12. With this structure, the motor 14 is capable of rotating the electrode 12 via the gear 15 so that the electrical contact between the electrode 12 and the scalp can be ensured. The motor 14 can be one that rotates the electrode 12 when the looseness of the electrical contact is detected. Thus, it is possible to automatically ensure the electrical contact.

Figure 6:
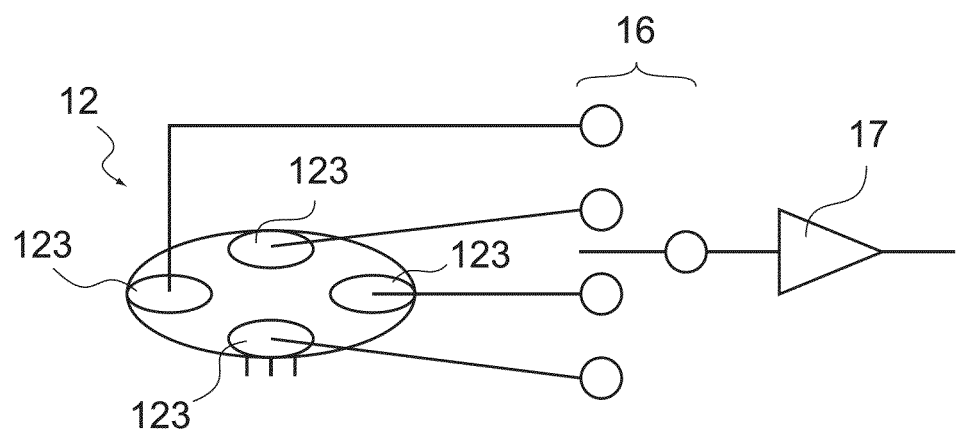
FIG. 6 is a schematic view showing a structure of an electrode of the electroencephalographic headset.

Further, the electrode 12 may be structured as follows. FIG. 6 is a schematic view showing a structure of the electrode 12. As shown in the figure, the electrode 12 is separated into a plurality of electrode portions 123 to abut against the scalp. The electrode portions 123 are arranged in proximity to each other. Each of the electrode portions 123 is connected to a changing switch 16 so that outputs from the electrode portions 123 to be outputted to an amplifier 17 can be changed to one another.

With such a configuration of the electrode 12, if the electrical contact of any of the electrode portions 123 with the scalp is not good, that electrode portion can be changed to another electrode portion for use. The change operation of the electrode portions will be described later.

Figure 7:
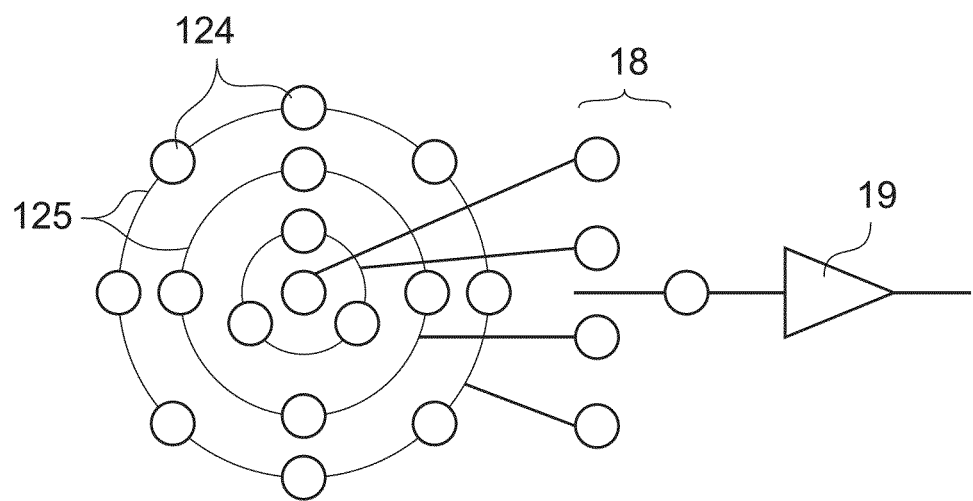
FIG. 7 is a schematic view showing a structure of an electrode of the electroencephalographic headset.

In addition, the electrode 12 may be structured as follows. FIG. 7 is a schematic view showing a structure of the electrode 12. As shown in the figure, the electrode 12 is separated into a plurality of electrode portions 124 to abut against the scalp and the electrode portions 124 are concentrically connected to each other. Hereinafter, those electrode portions 124 concentrically connected to each other are referred to as concentric electrode groups 125. The electrode portions 124 in each concentric electrode group 125 are connected to a changing switch 18 so that outputs from the concentric electrode groups 125 to be outputted to an amplifier 19 can be changed to one another.

With such a configuration of the electrode 12, if the electrical contact of any of the concentric electrode groups 125 with the scalp is not good, the concentric electrode group 125 can be changed to another concentric electrode group 125 for use. The change operation will be described later.

[Operation of Electroencephalographic Headset]

Figure 8:
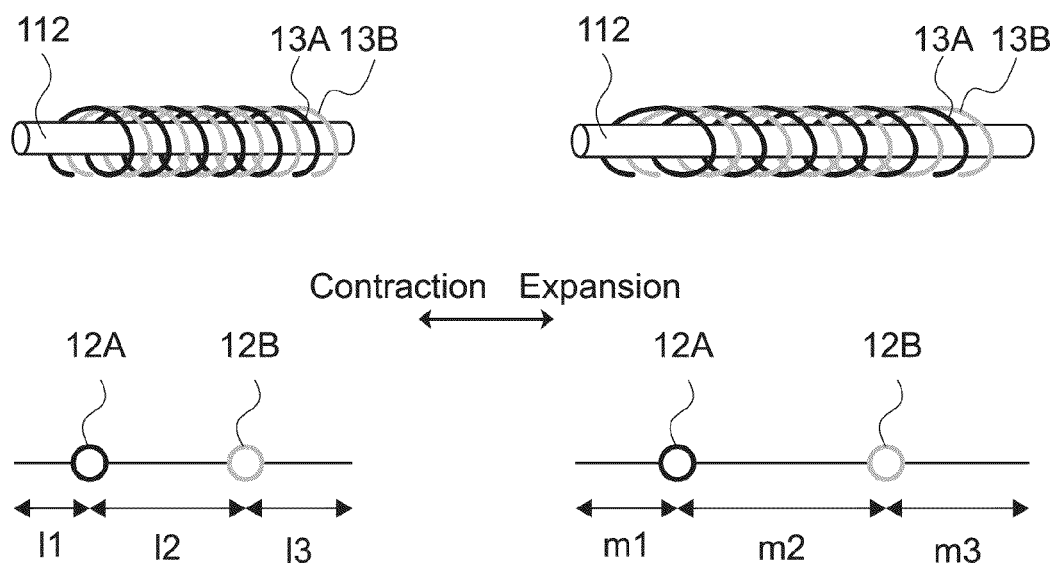
FIG. 8 is a schematic view showing expansion and contraction actions of an expanding and contracting wire of the electroencephalographic headset.

The operation of the electroencephalographic headset 1 will be described. As described above, when the electroencephalographic headset 1 is attached to the head of the user, the expanding and contracting wires 112 expand corresponding to the head size. FIG. 8 is a schematic view showing expansion and contraction actions of the expanding and contracting wire 112. As shown in the figure, the expanding and contracting wire 112 is provided with two electrodes of an electrode 12A and an electrode 12B. A wiring 13A and a wiring 13B are connected to the electrode 12A and the electrode 12B, respectively.

Provided that intervals of the electrode 12A and the electrode 12B when the expanding and contracting wire 112 contracts are indicated by 11, 12, and 13 and the intervals of the electrode 12A and the electrode 12B when the expanding and contracting wire 112 expands are indicated by m1, m2, and m3, 11:12:13 is equal to m1: m2: m3. In this manner, in the electroencephalographic headset 1, irrespective of the degree of expansion and retraction of the expanding and contracting wire 112, the electrodes 12 can be in the defined placement.

Figure 9:
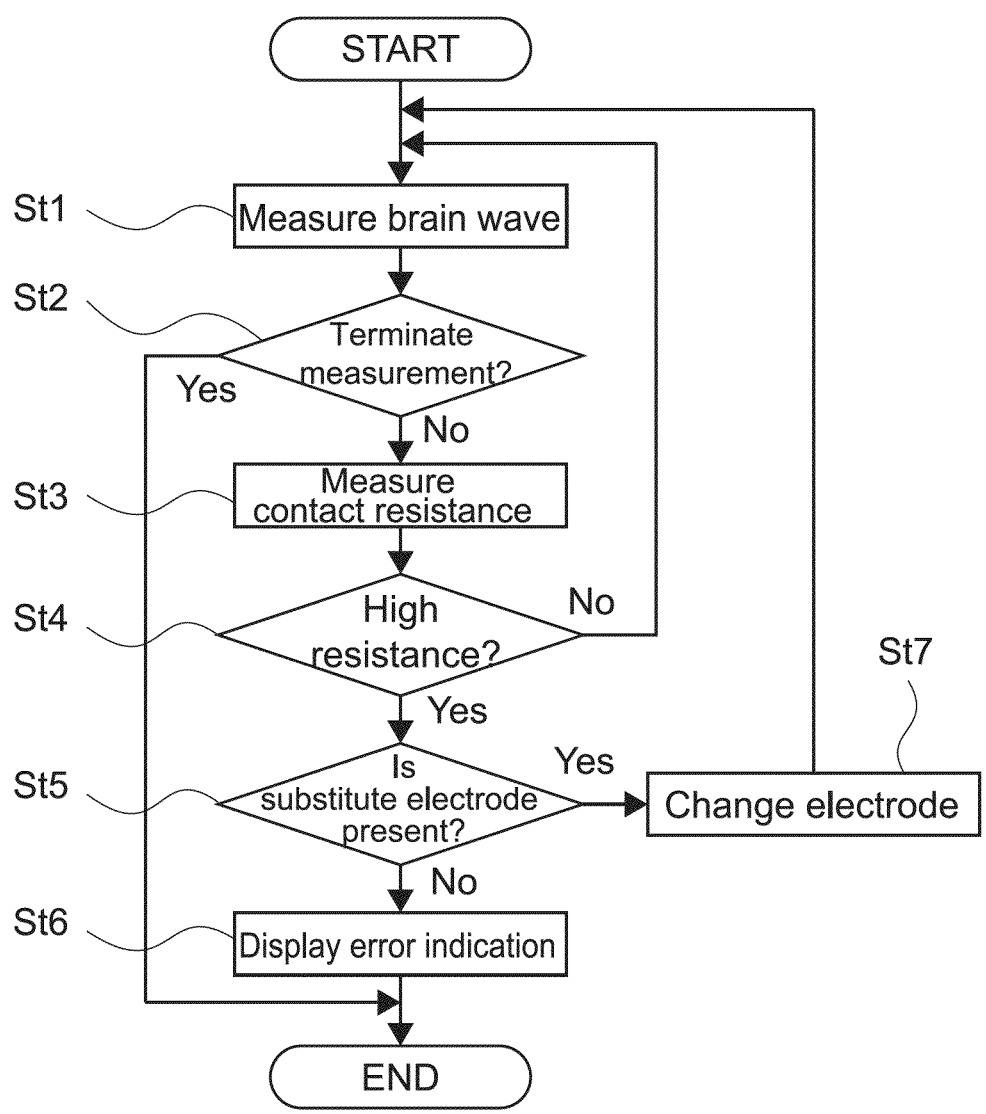
FIG. 9 is a flowchart showing an operation of improving electrical contact of the electroencephalographic headset.

As described above, in the electroencephalographic headset 1, when the electrical contact of one of the electrodes 12 with the scalp becomes loose, an operation of improving the electrical contact of the electrode 12 with the scalp can be performed. FIG. 9 is a flowchart showing the operation of improving the electrical contact.

In brain wave measurement (St1), when a predetermined time has elapsed, it is checked whether or not to terminate the brain wave measurement (St2). When the brain wave measurement is to be terminated (St2: Yes), the brain wave measurement is terminated. When the brain wave measurement is not to be terminated (St2: No), contact resistance measurement (St3) is performed.

When the contact resistance is high resistance (St4: Yes), it is determined that the electrical contact between the electrode 12 and the scalp is loose and it is checked whether or not a substitute electrode is present (St4). On the other hand, when the contact resistance is low resistance (St4: No), it is determined that the electrical contact between the electrode 12 and the scalp is good, the processing returns to the brain wave measurement (St1).

When the substitute electrode (another electrode portion 123 or concentric electrode group) is present (St4: Yes), the electrode is changed thereto (St5). The change of the electrode includes a change by the switch 16 or the switch 18 and a rotation of the electrode 12 by the motor 14. When the substitute electrode is not present (St4: No), an error indication showing that the electrical contact of the electrode 12 is loose is displayed (St6) and the brain wave measurement is terminated.

In this manner, in the electroencephalographic headset 1, the contact resistance measurement monitors the electrical contact between the electrode 12 and the scalp and, when the electrical contact is deteriorated, the electrical contact can be improved.

As described above, the electroencephalographic headset 1 according to this embodiment is easy to attach and is capable of placing the electrodes in correct positions.

(Second Embodiment)

An electroencephalographic headset according to a second embodiment of the present disclosure will be described. It should be noted that, in descriptions of this embodiment, the same description as that of the first embodiment may be omitted.

Figure 10:
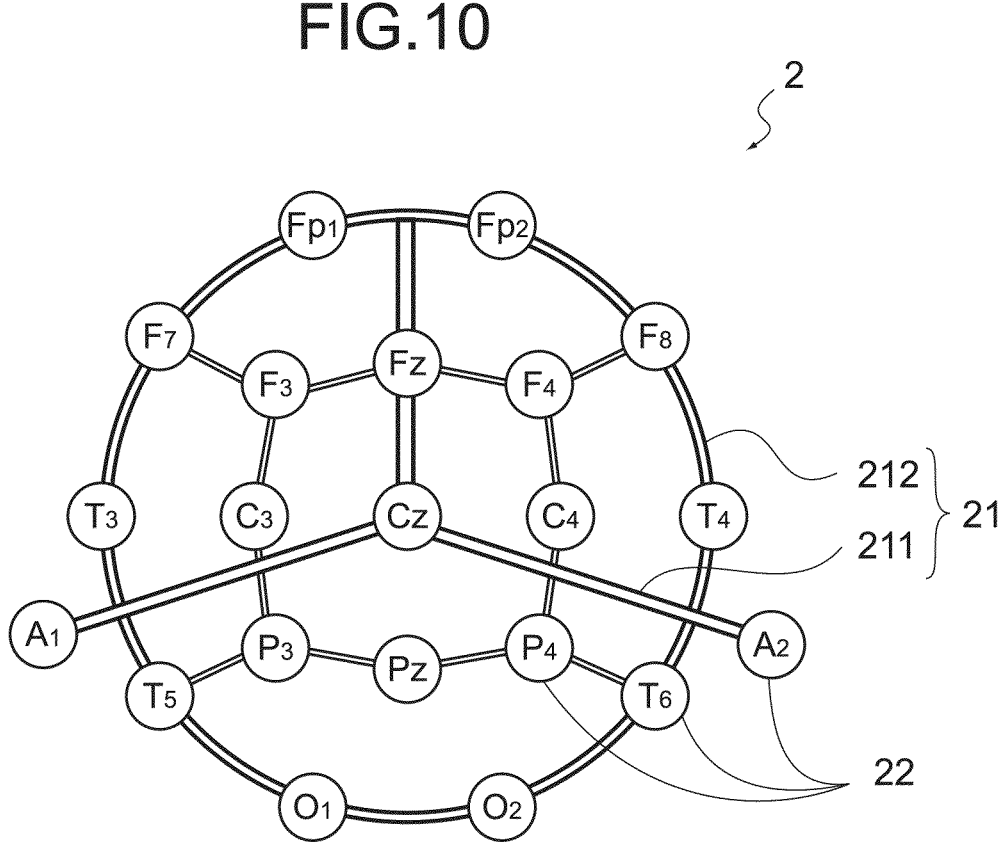
FIG. 10 is a schematic view showing a configuration of an electroencephalographic headset according to a second embodiment of the present disclosure.
Figure 11:
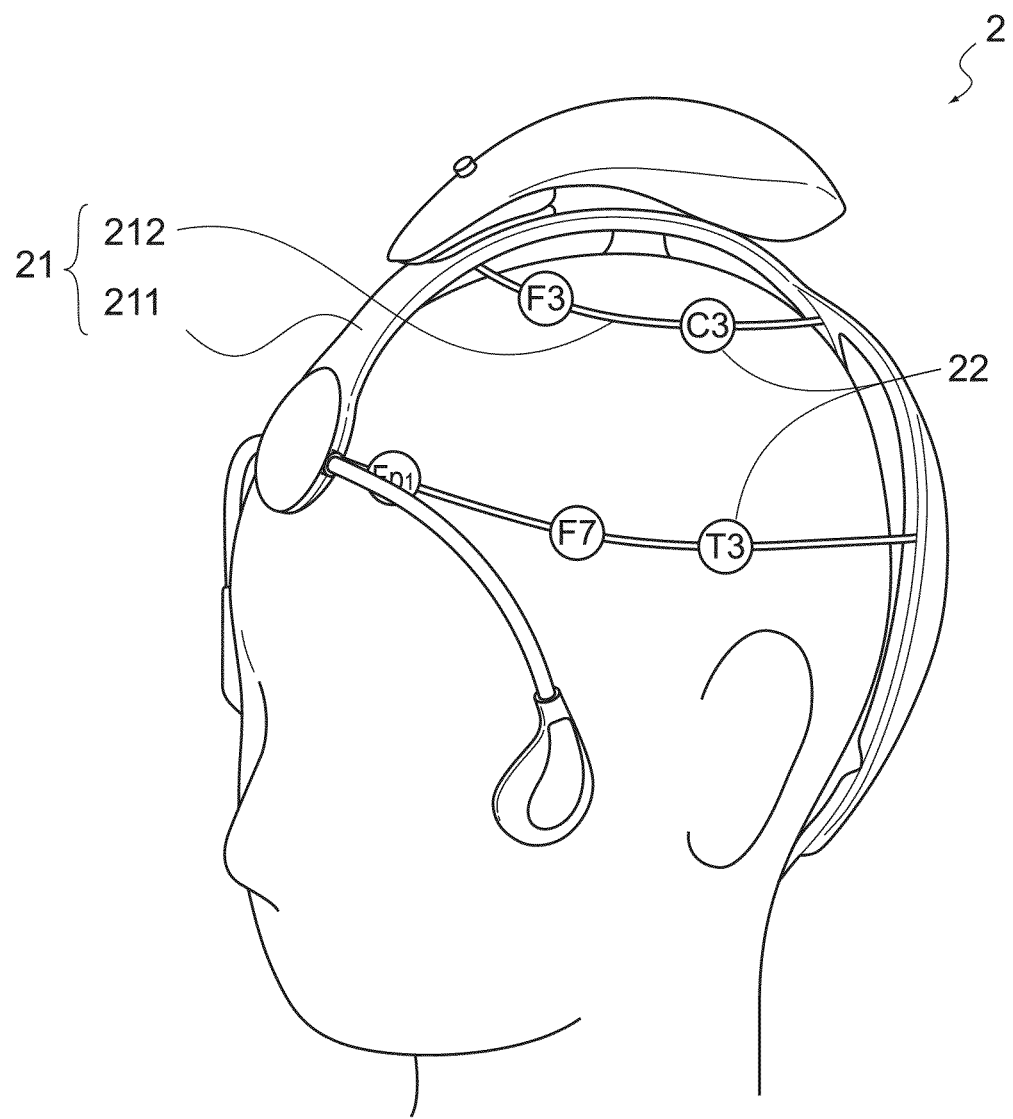
FIG. 11 is a schematic view showing a configuration of the electroencephalographic headset.

FIGS. 10 and 11 are views each showing a configuration of an electroencephalographic headset 2 according to this embodiment. FIG. 10 is a top view thereof and FIG. 11 is a schematic view of the electroencephalographic headset 2 attached to the user. As shown in those figures, the electroencephalographic headset 2 is constituted of a supporter 21 and electrodes 22. The supporter 21 is attachable to the head of the user. The plurality of electrodes 22 are provided in predetermined positions of the supporter 21.

The supporter 21 is constituted of a head-fixing arm 211 and a plurality of expanding and contracting wires 212. The head-fixing arm 211 is constituted of three arms having a shape corresponding to the head of the user and is alone attachable to the head of the user. Although not particularly limited, a material of the head-fixing arm 211 can be, for example, a lightweight material such as a synthetic resin. It should be noted that the shape of the head-fixing arm 211 is not limited to that shown here and other shapes capable of holding the head of the user can be adopted.

As shown in FIG. 10, the expanding and contracting wires 212 are concentrically connected to the head-fixing arm 211. The expanding and contracting wires 212 only need to be linear members each having expansion and contraction properties and there are no particular limitations. It should be noted that the expanding and contracting wires 212 may be straight when the electroencephalographic headset 2 is not attached to the head of the user and only need to be concentric when attached thereto.

The electrodes 22 are arranged in defined positions on the supporter 21. The electrodes 22 may be provided not only on the expanding and contracting wires 212 but also on the head-fixing arm 211. Although not particularly limited, the electrode placement can be placement according to the international 10-20 system being the standard electrode placement in the current brain wave measurement that is shown in FIG. 4.

The configuration of the electrodes 22 is not particularly limited and the configuration described in the first embodiment can be adopted. Also, in this embodiment, when the supporter 21 is attached to the head of the user, the expanding and contracting wires 212 expand and contract so that the electrodes 22 can be placed in the defined positions.

As described above, the electroencephalographic headset 2 according to this embodiment is easy to attach and is capable of placing the electrodes in correct positions.

The present disclosure is not limited only to the above-mentioned embodiments and can be changed without departing from the gist of the present disclosure. It should be noted that the present disclosure may also be configured as follows.

(1) An electroencephalographic headset, including:
  a supporter that includes expanding and contracting wires each having expansion and contraction properties and is to be attached to a head of a user by expansion and contraction of each of the expanding and contracting wires; and
  a plurality of electrodes that are provided to the supporter in defined placement.

(2) The electroencephalographic headset according to (1), in which
  the supporter is constituted of
    an annular frame to be placed around the head of the user, and
    the expanding and contracting wires that are radially connected to each other and are connected to the frame.

(3) The electroencephalographic headset according to (1) or (2), in which
  the supporter is constituted of
    a head-fixing arm to be attached to the head of the user, and
    the expanding and contracting wires that are concentrically connected to the head-fixing arm.

(4) The electroencephalographic headset according to any one of (1) to (3), in which
  the electrode is constituted of
    a core that is formed of silver/silver chloride with each of the expanding and contracting wires being a center axis, and
    an elastic member that is wound around the core in a cylindrical form and impregnated with an electrolytic solution.

(5) The electroencephalographic headset according to any one of (1) to (4), further including
  a driving unit configured to rotate one of the electrodes when electrical contact between the electrode and a scalp of the user is loose, the electrical contact being detected based on contact resistance of the electrode.

(6) The electroencephalographic headset according to any one of (1) to (5), in which
  the defined placement is electrode placement according to an international 10-20 system, and
  the expanding and contracting wires are connected corresponding to the electrode placement according to the international 10-20 system.

The present disclosure contains subject matter related to that disclosed in Japanese Priority Patent Application JP 2011-219132 filed in the Japan Patent Office on October 3, 2011, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An electroencephalographic headset, comprising:
   a supporter that includes expanding and contracting wires each having expansion and contraction properties and is to be attached to a head of a user by expansion and contraction of each of the expanding and contracting wires; and
   a plurality of electrodes that are provided to the supporter in defined placement,
   wherein each of the plurality of electrodes is constituted of:
      a core that is formed of silver/silver chloride with each of the expanding and contracting wires being a center axis, and
      an elastic member that is wound around the core in a cylindrical form and impregnated with an electrolytic solution.

2. The electroencephalographic headset according to claim 1, wherein the supporter is constituted of:
   an annular frame to be placed around the head of the user, and
   the expanding and contracting wires that are radially connected to each other and are connected to the annular frame.

3. The electroencephalographic headset according to claim 1, wherein the supporter is constituted of
   a head-fixing arm to be attached to the head of the user, and
   the expanding and contracting wires that are concentrically connected to the head-fixing arm.

4. The electroencephalographic headset according to claim 1, further comprising a driving unit configured to rotate one of the plurality of electrodes when electrical contact between the one of the plurality of electrodes and a scalp of the user is loose, the electrical contact being detected based on contact resistance of the one of the plurality of electrodes.

5. The electroencephalographic headset according to claim 1, wherein
   the defined placement is electrode placement according to an international 10-20 system, and
   the expanding and contracting wires are connected corresponding to the electrode placement according to the international 10-20 system.

* * * * *